(12) United States Patent
Shapiro

(10) Patent No.: US 10,806,790 B1
(45) Date of Patent: Oct. 20, 2020

(54) PAIN THERAPY CREAM WITH DEEP TISSUE DELIVERY SYSTEM

(71) Applicant: Scott Shapiro, Henderson, NV (US)

(72) Inventor: Scott Shapiro, Henderson, NV (US)

( * ) Notice: Subject to any disclaimer, the term of this patent is extended or adjusted under 35 U.S.C. 154(b) by 805 days.

(21) Appl. No.: 14/539,694

(22) Filed: Nov. 12, 2014

Related U.S. Application Data

(60) Provisional application No. 61/902,984, filed on Nov. 12, 2013.

(51) Int. Cl.
| | | |
|---|---|---|
| *A61K 47/10* | (2017.01) | |
| *A61K 31/165* | (2006.01) | |
| *A61K 36/53* | (2006.01) | |
| *A61K 9/06* | (2006.01) | |
| *A61K 9/00* | (2006.01) | |
| *A61K 45/06* | (2006.01) | |
| *A61K 31/435* | (2006.01) | |
| *A61K 31/10* | (2006.01) | |

(52) U.S. Cl.
CPC ............ *A61K 47/10* (2013.01); *A61K 9/0014* (2013.01); *A61K 9/06* (2013.01); *A61K 31/10* (2013.01); *A61K 31/165* (2013.01); *A61K 31/435* (2013.01); *A61K 36/53* (2013.01); *A61K 45/06* (2013.01)

(58) Field of Classification Search
None
See application file for complete search history.

(56) References Cited

U.S. PATENT DOCUMENTS

2012/0164087 A1 * 6/2012 Carter ...................... A61K 8/64
424/60

FOREIGN PATENT DOCUMENTS

| EP | 1000618 A1 * 5/2000 ........... A61K 31/165 |
| JP | 2002161043 A * 6/2002 |

* cited by examiner

*Primary Examiner* — Aaron J Kosar
(74) *Attorney, Agent, or Firm* — Verrill Dana, LLP

(57) ABSTRACT

The invention provides a pain therapy cream comprising an anhydrous topical delivery formulation for percutaneous absorption comprising an anhydrous carrier medium, a chemical exfoliant, a penetration enhancer, and one or more pain killing agent selected from the group consisting of an analgesic, anesthetic, anti-inflammatory, or antipruritic agent, a phytochemical and other painkilling active ingredients, and methods of using the pain therapy cream.

15 Claims, No Drawings

PAIN THERAPY CREAM WITH DEEP TISSUE DELIVERY SYSTEM

BACKGROUND OF THE INVENTION

Field of the Invention

The invention relates to the treatment of arthritis and pain. More particularly, the invention relates to topical formulations for such treatment.

Summary of the Related Art

Pain medications delivered via a topical cream have significant advantages over oral dosage forms (pills, capsules) and patches. Compared to pills and capsules, for example, topical delivery avoids first-pass GI and hepatic metabolism reducing the incidence and severity of adverse side effects in the stomach and liver, provides for consistent control of drug absorption, achieves therapeutic blood levels with lower absorbed dosages, results in improved patient compliance and offers the ability to deliver drugs more selectively to a specific site.

Patches have been used to deliver pain medication; however topical creams can deliver drugs with larger molecular weights and higher daily dosage requirements, without limitations related to poor patch adhesion or discomfort and with improved patient compliance.

Unfortunately, topical pain creams have had significant limitations due to suboptimal deep tissue penetration kinetics. The percutaneous absorption of drugs and its subsequent deep tissue delivery is a complex process. Because of the nature of the skin and its role as a barrier for keeping unwanted substances out of the body, there have been limitations with topical drug absorption. In many cases, a drug's properties, including molecular size and polarity, have limited its capacity to penetrate the skin. Current pain creams generally treat mild to moderate arthritis and pain and the duration of the pain relief is relatively short requiring reapplication every 3-4 hours. There is, therefore, a need for a topical pain cream that can improve deep tissue penetration so as to relieve arthritis and pain to a greater degree (moderate to severe pain) and for a longer period of time thus requiring fewer daily applications.

BRIEF SUMMARY OF THE INVENTION

The invention relates to the treatment of arthritis and pain. More particularly, the invention relates to the treatment of arthritis and pain through a topical delivery system. The invention provides a pain therapy cream with a deep tissue delivery system.

In a first aspect, the invention provides a pain therapy cream comprising an anhydrous topical delivery formulation for percutaneous absorption. The formulation comprising an anhydrous carrier medium, a chemical exfoliant, a penetration enhancer, and an analgesic, anesthetic, anti-inflammatory, antipruritic or painkilling active ingredient. The pain therapy cream with deep tissue delivery system according to the invention is a novel multi-mechanistic topical formulation that is designed to enable deep percutaneous penetration of painkilling therapeutic agents into muscles and joints via enhanced skin penetration and increased drug bioavailability. More effective drug delivery to deep tissues results in a longer and more profound painkilling effect.

In a second aspect, the invention provides a method for treating pain comprising topically administering to the skin the pain therapy cream according to the first aspect of the invention.

DETAILED DESCRIPTION OF THE PREFERRED EMBODIMENTS

The invention relates to the treatment of arthritis and pain. More particularly, the invention relates to the treatment of arthritis and pain through a topical delivery system. The invention provides a pain therapy cream with a deep tissue delivery system.

In a first aspect, the invention provides a pain therapy cream comprising an anhydrous topical delivery formulation for percutaneous absorption. The formulation comprising an anhydrous carrier medium, a chemical exfoliant, a penetration enhancer, and an analgesic, anesthetic, anti-inflammatory, or antipruritic agent, a phytochemical, (which can act as an analgesic or anti-inflammatory agent, or both), or other painkilling active ingredient.

Preferred anhydrous carrier media include, without limitation, esters, amides, ethoxylated fats, mineral oil, petrolatum, vegetable oils, animal fats, triglycerides, polyols, urea, glycerin, propylene glycol and sorbitol. In some embodiments, the carrier medium is glycerin, and the glycerin is present in a concentration of 10%-40%.

Preferred penetration enhancers include, without limitation, azone, urea, pyrrolidones, essential oils, terpenes and terpenoids, oxazolidinones, propylene glycol, epidermal enzymes, oleic acid, dimethyl isosorbide, sulphoxides, dimethylsulfoxide, dimethylsulfone, ethanol, diethylene glycol monoethyl ether, hyaluronic acid, chitin, mucopolysaccharides, fatty acids, linoleic acid, alpha linoleic acid, cod liver oil, menthol, menthol derivatives, squalene, glycerol derivatives, glycerol monoethers; chamomile flavones apigenin, lutrolin, and 7-O-beta-glucoside.

In some embodiments, the penetration enhancer acts through one or more of the following mechanisms: increasing the fluidity of the stratum corneum lipids and reducing the diffusional resistance to permeants; removing intercellular lipids and dilation between adherent cornified cells; increasing the thermodynamic activity of drugs in vehicles; exfoliating stratum corneum cell membranes; dissociating adherent cornified cells and elimination of the barrier function.

In some embodiments, the chemical exfoliant is alpha hydroxy acid (AHA) or beta hydroxy acid (BHA, salicylic acid), or combinations thereof.

In some embodiments, the analgesic agent includes, without limitation, one or more of camphor, menthol, capsaicin, capsicum, capsicum oleoresin, methyl salicylate, trolamine salicylate, salicylates, histamine dihydrochloride, methyl nicotinate, lidocaine, lidocaine hydrochloride, arnica, aspirin, diclofenac, ibuprofen, naproxen, ketoprofen, glucosamine sulfate, chondroitin, niacin, niacinamide, methylsulphonylmethane (MSM). In some embodiments, the analgesic agent is a central analgesic, including, without limitation, tramadol. In some embodiments, the analgesic agent is capsaicin, capsicum, or capsicum oleoresin. In some embodiments, the analgesic agent is capsaicin.

In some embodiments, the anti-inflammatory agent is a non-steroidal anti-inflammatory drug (MAID), including without limitation, aspirin (acetylsalicylic acid), diclofenac, diflunisal, etodolac, fenoprofen, flurbiprofen, ibuprofen, indomethacin, ketoprofen, ketorolac, meclofenamate, mefenamic acid, meloxicam, nabumetone, naproxen and naproxen sodium, oxaprozin, phenylbutazone, piroxicam, sulindac, tolmetin, celecoxib and acetaminophen. When the NSAID is aspirin, ibuprofen, acetaminophen, or a cox-2 inhibitor, the formulation does not include micronized niacin.

Other pain killing active ingredients include narcotic pain medications, including, without limitation buprenorphine, butorphanol, codeine, hydrocodone, hydromorphone, levorphanol, meperidine, methadone, mentanyl, morphine, nalbuphine, oxycodone, oxymorphone, pentazocine and propoxyphene.

Phytochemicals include, without limitation, *Harpagophytum procumbens* (Devil's Claw root extract), *Harpagophytum zeyheri*, shark cartilage, willow bark, unsaponifiable avocado soybean fraction, *Boswellia serrata* gum resin, bromelain, ginger, curcumin and arnica. In some preferred embodiments, the phytochemical is *Harpagophytum procumbens* or *Harpagophytum zeyheri*. In some preferred embodiments, the phytochemical is *Harpagophytum procumbens*.

Any analgesic, anesthetic, anti-inflammatory, phytochemical, antipruritic or other painkilling agent can be used alone or in any combination with any one or more other analgesic, anesthetic, anti-inflammatory, phytochemical, antipruritic or other painkilling agent. The formulation may further include vasodilators. Vasodilation is the widening of blood vessels resulting from relaxation of smooth muscle cells within the vessel walls. Vasodilators, once in the dermal layer of the skin, act to expand or dilate the capillaries and other blood vessels in and beneath the dermal layer, resulting in an increase in blood flowing into and away from the site of system application. Capillary vasodilation (for example by methylnicotinic acid, L-arginine, or nicotinic acid) increases the rate of diffusion of the therapeutic drug across the capillary wall and into the systemic circulation. Vasodilators include, without limitation, acetylcholine, amrinone, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di-isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, methyl salicylate, naftidrofuryl oxalate, nicametate citrate, niceritrol, nicoboxil, nicofuranose, nicotinyl alcohol, nicotinic acid, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, xanthinol nicotinate, diazoxide, hydralazine, minoxidil and sodium nitroprusside. Some vasodilators are centrally acting agents, including, without limitation, clonidine, quanaberz and methyl dopa. Some vasodilators are alpha-adrenoceptor blocking agents, including, without limitation, indoramin, phenoxybenzamine, phentolamine and prazosin. Some vasodilators are adrenergic neuron blocking agents, including, without limitation, bedmidine, debrisoquine and guanethidine. Some vasodilators are ACE inhibitors, including, without limitation, benazepril, captopril, cilazapril, enalapril, fosinopril, lisinopril, perindopril, quinapril and ramipril. Some vasodilators are ganglion-blocking agents, including, without limitation, pentolinium and trimetaphan. Some vasodilators are calcium channel blockers, including, without limitation, amlodipine, diltiazem, felodipine, isradipine, nicardipine, nifedipine, nimodipine and verapamil. Some vasodilators are prostaglandins, including, without limitation, prostacyclin, thromboxane A2, L-arginine, leukotrienes, PGA, PGA1, PGA2, PGE1, PGE2, PGD, PGG and PGH. Some vasodilators are Angiotension II analogs including, without limitation, saralasin. Other vasodilators including, without limitation, nitroglycerin, labetalol, thrazide, isosorbide dinitrate, pentaerythritol tetranitrate, digitalis, and diazoxide can serve exclusively as vasodilation agents, or may also serve another function to the delivery complex such as the penetration agent or the active drug agent. One or more vasodilators or chemically modified vasodilators may be used in the delivery complex at any one time for one formulation for the purpose of transdermally delivering an active drug molecule or agent. The delivery complex may contain one or more different vasodilators in the same complex to achieve varying and different degrees and modes of vasodilation.

Some formulations contain vasoconstrictors. Vasoconstriction is the narrowing of the blood vessels resulting from contraction of the muscular wall of the vessels. Vasoconstrictors restrict systemic drug absorption as a result of intense subcutaneous vasoconstriction, as well as direct hydrostatic compression of capillaries and veins. Vasoconstrictors include, without limitation, catecholamines, norepinephrine, epinephrine, isoproterenol, dopamine, ephedrine, phenylisopropylamines, phenylephrine, amphetamine, metraminol, methoxamine, lysergic acid, lisergic acid diethylamine. The term "vasoconstrictor", as used herein, refers to a composition of matter or mixture that narrows the lumen of blood vessels and, hence, reduces peripheral blood flow. Other examples of suitable vasoconstrictors include, without limitation, amidephrine, cafaminol, cyclopentamine, deoxyepinephrine, epinephrine, felypressin, indanazoline, metizoline, midodrine, naphazoline, nordefrin, octodrine, ornipressin, oxymethazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and mixtures thereof.

Other bioactive substances may be present in the formulation, including, without limitation, glucosamine sulfate, chondroitin, glycosaminoglycans, methylsulfonylmethane (MSM), niacinamide, niacin, niacin derivatives, ascorbic acid, ascorbic acid derivatives, omega-3 fatty acids, evening primrose oil, shark cartilage and S-adenosylmethionine.

It is an object of the invention to provide improved performance (longer and more profound therapeutic effect) relative to existing topical arthritis and pain treatment formulations by improving deep percutaneous penetration into muscles and joints.

Among these improvements are:
1. Anhydrous formulation: The formulation is substantially water-free. Non-aqueous solvents increase skin penetration of the drug substance. A water-based vehicle cannot effectively deliver drugs through the water resistant stratum corneum.
2. High drug concentration gradient: A high drug concentration gradient across the skin increases the thermodynamic activity of the drug forcing it out of the vehicle and across the stratum corneum increasing drug permeation and drug penetration rate.
3. Wet nanosizing process: As particle size decreases the surface area of a material grows rapidly. The rate of solubilization of a material is a function of exposed surface area and so the smaller the particles and the greater the surface area the more easily and rapidly it is absorbed. Coating the drug particles in a skin penetration-enhancing oil or solvent via a proprietary "wet"

nanosizing process results in smaller nanoparticles with increased stability and greater skin penetration.

4. Hydration of the skin: High glycerin content causes transepidermal water movement from the deeper layers of the skin to the stratum corneum which is comprised of only 20% water. Stratum corneum hydration increases drug penetration. Water opens up the compact structure of the horny layer. Water cannot be imparted to the skin from a water-based vehicle because skin is water resistant.
5. Exfoliants: The thickness of the stratum corneum is a rate limiting barrier to drug penetration across the skin. Chemical exfoliation thins the stratum corneum increasing drug penetration and bioavailability.
6. Chemical Penetration enhancers: Reversibly alters the physiochemical nature of the stratum corneum to reduce its diffusional resistance by creating temporary miniature channels allowing for greater skin penetration of the drug.
7. Long residence time on skin: The longer the formulation remains in contact with the skin, the greater the drug absorption.
8. Poorly Soluble/Insoluble Drugs: Particle-size reduction to the nanometer scale increases the rate of dissolution substantially enhancing skin penetration of poorly soluble drugs and increases percutaneous absorption of insoluble drugs by enlarging the effective surface area.
9. Hydrophilic Drugs: Hydrophilic molecules prefer the water in skin to the anhydrous vehicle and will partition out of the vehicle and into the skin increasing drug flux. Nanoparticles are solubilized on contact with a hydrated stratum corneum.
10. Vasodilators/Vasoconstrictors: Vasodilators and vasoconstrictors enable targeted drug delivery. Vasodilators, once in the dermal layer of the skin, act to expand or dilate the capillaries and other blood vessels in and beneath the dermal layer, resulting in an increase in blood flowing into and away from the site of system application. Capillary vasodilation (for example, by methylnicotinic acid, L-arginine, or nicotinic acid) increases the rate of diffusion of the therapeutic drug across the capillary wall and into the systemic circulation. Vasoconstrictors optimize local drug delivery and restrict systemic drug absorption as a result of intense subcutaneous vasoconstriction, as well as direct hydrostatic compression of capillaries and veins.

In a second aspect, the invention provides a method for treating pain comprising topically administering to the skin the pain therapy cream according to the first aspect of the invention. In some embodiments, the pain therapy cream is applied locally to the area of pain and the painkilling therapeutic agents reach deep tissues via direct penetration. In some embodiments, the pain therapy cream is applied to any convenient area of the skin and the painkilling therapeutic agents reach deep tissues via systemic redistribution.

The following examples are intended to further illustrate certain embodiments of the invention and are not intended to limit the scope of the invention.

EXAMPLE 1

Preparation of an Exemplary Pain Therapy Cream

This pain therapy cream contains 0.075% purified capsaicin, 5% *Harpagophytum* extract, 5% niacinamide, 5% methylsulfonylmethane, 15% L-ascorbic acid, 30% glycerin, 5% propylene glycol (penetration enhancer) and 2% salicylic acid (chemical exfoliant). *Harpagophytum* extract is a brown fibrous powder and thus difficult to administer topically. The *Harpagophytum* extract powder is added to a liquid such as a vegetable oil or solvent forming a suspension that is 25% *Harpagophytum* extract to 75% liquid. The suspension is milled in a horizontal bead mill (Netzsch Microcer) with $ZrO_2$ 0.5 mm beads at an agitator speed of 2200 rpm and a flow rate of 0.250 Kg/min for 240 minutes. The mean particle size of the *Harpagophytum* extract as measured by laser diffraction (Horiba LA-950 Laser Particle Size Analyzer) is <2 microns. The resultant slurry is added to the cream mixture under slow agitation (<200 rpm) at a temperature <50° C. The finished cream is viscous (150,000 cps) smooth and beige in color.

EXAMPLE 2

Application of Pain Therapy Cream for Localized Pain

A thin film of cream is applied to the painful area and rubbed in until fully absorbed. For optimum relief application is 2 to 3 times daily. Best results typically occur after 1 to 2 weeks of continuous use. Unless treating hands, hands should be washed with soap and water immediately after use. The cream may cause a burning sensation, which is normal and related to the way it works. With regular use, this sensation generally disappears within several days. Cream should not be applied to open wounds or to damaged or cracked skin, or allowed to contact mucous membranes, eyes, or contact lenses. If this occurs, the affected area should be rinsed thoroughly with water. Cream should not be applied immediately before or after activities such as showering, hot tub therapy, or strenuous exercise. Heat should not be applied to the treated areas immediately before or after use. Do not tightly wrap or bandage the treated area. Store at 68°-77° F.

EXAMPLE 3

Comparative Example

The purpose of this study was to compare the safety and efficacy of a topical cream (CellMedics®) containing 0.075% w/w capsaicin and 5% w/w *Harpagophytum* extract vs. oral diclofenac 50 mg tablets over a 12-week treatment course in relieving the symptoms of primary osteoarthritis (OA) of the knee, in a randomized, double-blind, double-dummy, parallel-group study. Eligible patients included men and nonpregnant women between the ages of 45-75 with symptomatic OA of the knee of at least three months duration. All patients had knee OA as defined by the American College of Rheumatology global functional class I, II, or III. Patients were excluded if they had secondary arthritis related to syphilitic neuropathy, ochronosis, psoriasis, metabolic bone disease, or acute trauma; chondrocalcinosis with a history of pseudogout; fibromyalgia; previous major surgery to the knee or recommendation for knee replacement/reconstruction; current or recent corticosteroid use; topical product use at the application site; history of sensitivity to any of the study drugs or other NSAIDs; severe, uncontrolled cardiac, renal, hepatic, or other systemic disease; recent stomach ulcer or GI bleeding; history of alcohol or drug abuse; lactation; or concomitant skin diseases at the application site. Concomitant use of other analgesic medications was prohibited during the study. The protocol was a 12-week, randomized, double-blind, double-dummy, parallel-group comparative study. Patients were assessed at the initial screening visit and those who met the entry criteria discontinued NSAID treatment for a washout period of 3-10 days before the baseline visit. Following the screening and washout periods, each eligible patient attending the baseline visit was assigned a numbered study kit at the clinic. Study kits contained one of 2 randomly assigned treatments: (1) vehicle cream (CellMedics®) containing 0.075% w/w capsaicin and 5% w/w *Harpagophytum* extract (topical *Harpagophytum*) plus oral placebo tablet; or (2) diclofenac 50 mg tablet (oral diclofenac) plus a topical placebo cream (vehicle cream with no actives). Patients were instructed to apply a single 3 g measured dose of cream (150 mg of *Harpagophytum* and 2.25 mg of capsaicin in the active cream) from a metered pump dispenser around the affected knee and take a study tablet orally, 3 times daily for 12 weeks. Planned total daily dose for active treatments was 450 mg/6.75 mg of topical *Harpagophytum*/capsaicin or 150 mg oral diclofenac. The WOMAC osteoarthritis index, version 3.1 visual analog scale (VAS) was used to assess response to treatment at baseline and after week 12. Patients answered the WOMAC subscales of pain, stiffness, and physical function using a 48 hour recall period. For WOMAC, the VA scales were (best) 0-100 (worst). Safety analyses were conducted on all patients randomized into the trial. At week 12 visits, adverse events (AE) were recorded. The differences between baseline and week 12 were used to analyze changes in WOMAC scores. Statistical significance was assumed at p<0.05. The effect size was calculated by dividing the mean change from baseline with the standard deviation at baseline. Percent improvement was calculated by dividing week 12 change scores by baseline scores. A total of 72 patients were randomized to active treatment with either topical *Harpagophytum* (n=36) or oral diclofenac (n=36). All patients completed the full 12 weeks of treatment. The randomized treatment groups were comparable in age, sex, weight, height, and body mass (Table 1). Mean age of the patients was 63 years old and 54% were women. The duration of active treatment was 12 weeks for both treatment groups. Compliance data indicated that patients took over 96% of the planned dose of active topical *Harpagophytum* and oral diclofenac. Table 2 shows the results of changes in mean WOMAC scores from baseline to week 12 and effect size. The effect size (mean change from baseline divided by the standard deviation at baseline) for patients treated with topical *Harpagophytum* compared to patients treated with oral diclofenac were greater for pain (1.14 to 1.04), stiffness (0.94 to 0.90) and physical function (1.03 to 0.99). Mean baseline, change scores (week 12 minus baseline), and percent improvement for pain, stiffness and physical function are given in Table 3. Patients treated with topical *Harpagophytum* showed improvement in all efficacy variables of 53%-47% over baseline values while patients treated with oral diclofenac showed slightly less improvement of 49%-45%. The incidence of important drug-related AE is shown in Table 4. The AE exhibiting the greatest incidence were application-site dryness in the in the topical *Harpagophytum* group and abdominal pain (22.2%) in the oral diclofenac group. Patients treated with topical *Harpagophytum* experienced significantly fewer GI AE, including abdominal pain, constipation, dyspepsia, diarrhea, nausea, and flatulence. Oral diclofenac patients experienced edema (8.3%) and headaches (5.6%); none of the topical *Harpagophytum* patients experienced these AE. Patients treated with topical *Harpagophytum* had slightly higher application-site skin related AE compared to the oral diclofenac group using placebo cream. The greatest incidence was found for dry skin; 2 patients (5.6%) in the topical group vs. 1 patient (2.8%) in the oral group, which was judged mild and transient in all cases. One patient (2.8%) in both the topical *Harpagophytum* and oral diclofenac groups reported mild redness (erythema) which resolved within 24 hours of continued treatment in both cases.

TABLE 1

Demographic characteristics of treatment groups

| | Topical *Harpagophytum* n = 36 | Oral Diclofenac n = 36 |
|---|---|---|
| Age, yrs | 63 (10.43) | 62.4 (10.21) |
| Women, no. (%) | 20 (55%) | 19 (53%) |
| Weight, kg | 84 (17.4) | 85 (17.73) |
| Height, cm | 164.4 (10.4) | 165 (9.7) |
| Body mass index (kg/m2) | 31 (5.2) | 31 (5.4) |

Values are mean (SD) or n (%)

TABLE 2

Change in WOMAC subscales* from baseline to week 12 for knee for topical *Harpagophytum* and oral diclofenac treated groups.

| WOMAC subscale | Pain | Stiffness | Physical Function |
|---|---|---|---|
| Topical *Harpagophytum* n = 36 | | | |
| Baseline | 46.6 (21.58) | 47.98 (24.12) | 47.22 (21.38) |
| Baseline - week 12 change score | −24.68 (21.09) | −22.78 (22.79) | −22.09 (19.44) |
| Effect size | 1.14 | 0.94 | 1.03 |
| Oral Diclofenac n = 36 | | | |
| Baseline | 46.89 (22.08) | 48.26 (23.96) | 47.64 (22.16) |
| Baseline - week 12 change score | −22.87 (21.83) | −21.65 (22.71) | −21.87 (21.34) |
| Effect size | 1.04 | 0.90 | 0.99 |

WOMAC: Western Ontario and McMaster Universities osteoarthritis index
*WOMAC VA scales (best) 0- 00 (worst)
Statistical significance was assumed at p < 0.05

TABLE 3

Baseline and change scores at week 12 with percent improvement following treatment.

| | | | Baseline - Week 12 | | |
|---|---|---|---|---|---|
| Variable | Treatment Group | n | Baseline | Change Score | % Improvement |
| WOMAC Pain | Topical *Harpagophytum* | 36 | 46.60 | −24.68 | 52.96% |
| | Oral Diclofenac | 36 | 46.89 | −22.87 | 48.77% |
| WOMAC Stiffness | Topical *Harpagophytum* | 36 | 47.98 | −22.78 | 47.48% |
| | Oral Diclofenac | 36 | 48.26 | −21.65 | 44.86% |

TABLE 3-continued

Baseline and change scores at week 12 with percent improvement following treatment.

| Variable | Treatment Group | n | Baseline - Week 12 | | |
|---|---|---|---|---|---|
| | | | Baseline | Change Score | % Improvement |
| WOMAC Physical function | Topical *Harpagophytum* | 36 | 47.22 | −22.09 | 46.78% |
| | Oral Diclofenac | 36 | 47.64 | −21.87 | 45.91% |

WOMAC: Western Ontario and McMaster Universities osteoarthritis index

TABLE 4

Incidence of adverse events.

| Adverse Event | Topical *Harpagophytum* n = 36 | Oral Diclofenac n = 36 |
|---|---|---|
| Gastrointestinal (GI) | | |
| Abdominal pain | 1 (2.8%) | 8 (22.2%) |
| Constipation | 0 (0.0%) | 3 (8.3%) |
| Diarrhea | 0 (0.0%) | 6 (16.7%) |
| Dyspepsia | 1 (2.8%) | 9 (25.0%) |
| Flatulence | 0 (0.0%) | 6 (16.7%) |
| Nausea | 0 (0.0%) | 4 (11.1%) |
| Application site | | |
| Dry Skin | 2 (5.6%) | 1 (2.8%) |
| Erythema | 1 (2.8%) | 1 (2.8%) |
| Pruritis | 0 (0.0%) | 0 (0.0%) |
| Blisters | 0 (0.0%) | 0 (0.0%) |
| Other | | |
| Edema | 0 (0.0%) | 3 (8.3%) |
| Headache | 0 (0.0%) | 2 (5.6%) |

Values are number (%)

These results demonstrate that a topical cream (CellMedics®) containing 0.075% w/w capsaicin and 5% w/w *Harpagophytum* extract applied to the knee produces slightly greater efficacy vs. oral diclofenac 50 mg tablets in the symptomatic treatment of primary osteoarthritis of the knee. The WOMAC VA 3.1 osteoarthritis index, a validated assessment questionnaire and the most commonly used measure of function in OA trials, was used to assess responses to treatment. Patients treated with topical *Harpagophytum* showed greater improvement in all efficacy variables compared to patients receiving oral diclofenac, namely reduction of pain, stiffness, and physical dysfunction. Patients treated with topical *Harpagophytum* exhibited a significantly better overall safety profile compared to patients receiving oral diclofenac. Application-site skin related reactions, primarily dry skin which was deemed mild and transient in all cases, were slightly higher for the topical *Harpagophytum* group compared to the oral diclofenac group using placebo cream. The combination of greater safety and efficacy makes a topical cream (CellMedics®) containing 0.075% w/w capsaicin and 5% w/w *Harpagophytum* extract an advantageous alternative to oral diclofenac sodium in the treatment of OA of the knee.

What is claimed is:

1. An anhydrous pain therapy cream comprising an anhydrous topical delivery formulation for percutaneous absorption, comprising an anhydrous carrier medium, a chemical exfoliant, diethylene glycol monoethyl ether as a penetration enhancer, optionally one or more additional penetration enhancers selected from the group consisting of azone, urea, pyrrolidones, essential oils, terpenes and terpenoids, oxazolidinones, propylene glycol, epidermal enzymes, oleic acid, dimethyl isosorbide, sulphoxides, dimethylsulfoxide, dimethylsulfone, ethanol, hyaluronic acid, chitin, mucopolysaccharides, fatty acids, linoleic acid, alpha linoleic acid, cod liver oil, menthol, menthol derivatives, squalene, glycerol derivatives, and glycerol monoethers, and one or more pain killing agents selected from the group consisting of a narcotic pain medication, an analgesic, anesthetic, anti-inflammatory, or antipruritic agent, a phytochemical and other painkilling active ingredients.

2. The pain therapy cream according to claim 1, wherein the anhydrous carrier medium is selected from the group consisting of esters, amides, ethoxylated fats, mineral oil, petrolatum, vegetable oils, animal fats, triglycerides, polyols, urea, glycerin, propylene glycol and sorbitol.

3. The pain therapy cream according to claim 2, wherein the carrier medium is glycerin, and the glycerin is present in a concentration of 10%–40%.

4. The pain therapy cream according to claim 1, wherein the chemical exfoliant is alpha hydroxy acid (AHA) or beta hydroxy acid (BHA), or combinations thereof.

5. The pain therapy cream according to claim 1, wherein the analgesic agent is selected from the group consisting of camphor, menthol, capsaicin, capsicum, capsicum oleoresin, methyl salicylate, trolamine salicylate, salicylates, histamine dihydrochloride, methyl nicotinate, lidocaine, lidocaine hydrochloride, arnica, aspirin, diclofenac, ibuprofen, naproxen, ketoprofen, glucosamine sulfate, chondroitin, niacin, niacinamide, methylsulphonylmethane (MSM) and tramadol.

6. The pain therapy cream according to claim 5, wherein the analgesic agent is capsaicin, capsicum, or capsicum oleoresin, or combinations thereof.

7. The pain therapy cream according to claim 6, wherein the analgesic agent is capsaicin.

8. The pain therapy cream according to claim 1, wherein the anti-inflammatory agent is one or more non-steroidal anti-inflammatory drug (NSAID).

9. The pain therapy cream according to claim 8, wherein the NSAID is selected from the group consisting of aspirin (acetylsalicylic acid), diclofenac, diflunisal, etodolac, fenoprofen, flurbiprofen, ibuprofen, indomethacin, ketoprofen, ketorolac, meclofenamate, mefenamic acid, meloxicam, nabumetone, naproxen and naproxen sodium, oxaprozin, phenylbutazone, piroxicam, sulindac, tolmetin, celecoxib and acetaminophen, provided, however, that when the NSAID is aspirin, ibuprofen, acetaminophen, or a cox-2 inhibitor, the formulation does not include micronized niacin.

10. The pain therapy cream according to claim 1, wherein the phytochemical is selected from the group consisting of *Harpagophytum procumbens* (Devil's Claw root extract), *Harpagophytum zeyheri* extract, willow bark, unsaponifiable avocado soybean fraction, *Boswellia serrata* gum resin, bromelain, ginger, curcumin and arnica.

11. The pain therapy cream according to claim 10, wherein the phytochemical is *Harpagophytum procumbens* or *Harpagophytum zeyheri* extract.

12. The pain therapy cream according to claim 1, further comprising a vasodilator.

13. The pain therapy cream according to claim 1, further comprising a vasoconstrictor.

14. The pain therapy cream according to claim 1, further comprising a bioactive substance selected from the group consisting of glucosamine sulfate, chondroitin, glycosaminoglycans, methylsufonylmethane (MSM), niacinamide, niacin, niacin derivatives, ascorbic acid, ascorbic acid derivatives, omega-3 fatty acids, evening primrose oil, shark cartilage and S-adenosylmethionine.

15. The pain therapy cream according to claim 1, wherein the painkilling active ingredient is a narcotic pain medication selected from one or more of buprenorphine, butorphanol, codeine, hydrocodone, hydromorphone, levorphanol, meperidine, methadone, mentanyl, morphine, nalbuphine, oxycodone, oxymorphone, pentazocine and propoxyphene.

\* \* \* \* \*